United States Patent [19]
Willeke

[11] Patent Number: 5,949,001
[45] Date of Patent: Sep. 7, 1999

[54] METHOD FOR AERODYNAMIC PARTICLE SIZE ANALYSIS

[76] Inventor: Klaus Willeke, 147 Ritchie Ave., Cincinnati, Ohio 45215-2062

[21] Appl. No.: 09/024,341

[22] Filed: Feb. 17, 1998

[51] Int. Cl.$^6$ .................................................. G01N 15/02
[52] U.S. Cl. .......................................... 73/865.5; 356/336
[58] Field of Search ............................... 73/865.5, 28.04; 356/438, 439, 335, 336

[56] References Cited

U.S. PATENT DOCUMENTS

| | | | |
|---|---|---|---|
| 3,790,760 | 2/1974 | Stiller | 356/335 |
| 4,152,923 | 5/1979 | Courbon | 73/28.04 |
| 4,895,034 | 1/1990 | Poole | 73/865.5 |
| 5,796,480 | 8/1998 | Igushi | 356/336 |

*Primary Examiner*—Robert Raevis
*Attorney, Agent, or Firm*—Wood, Herron & Evans, L.L.P.

[57] ABSTRACT

A method is provided for measuring the aerodynamic particle size distribution of airborne particles by drawing the particles through a device which continuously or intermittently changes the aerodynamic cut of the particles entering an optical sensor. Optical sensing is performed by aerosol photometry or optical single particle size spectrometry. If aerosol photometry is used, the aerosol photometer becomes an aerodynamic particle size spectrometer by relating the aerosol photometer's output to the aerodynamic particle size fractions passing through the aerodynamic cut device. If optical single particle size spectrometry is used, the optical single particle counter becomes an aerosol particle size spectrometer by calibrating the optical sizes of the optical single particle counter relative to the aerodynamic particle sizes determined by the aerodynamic cut device.

12 Claims, 7 Drawing Sheets

FIG. 4A

AEROSOL CONCENTRATION, No/m$^3$ vs OPTICAL PARTICLE DIAMETER, $d_{opt}$, μm $rpm_0 = 0$

FIG. 4B

AEROSOL CONCENTRATION, No/m$^3$ vs OPTICAL PARTICLE DIAMETER, $d_{opt}$, μm $rpm_1$, $d_{a1}$

FIG. 4C

AEROSOL CONCENTRATION, No/m$^3$ vs OPTICAL PARTICLE DIAMETER, $d_{opt}$, μm $rpm_2$, $d_{a2}$

METHOD FOR AERODYNAMIC PARTICLE
SIZE ANALYSIS

CROSS-REFERENCES TO RELATED APPLICATIONS

U.S. Patent Documents:
U.S. Pat. No. 4,633,714 January 1987 Mazumder et al. "Aerosol Particle Charge and Size Analyzer" 73/596

U.S. Pat. No. 5,296,910 March 1994 Cole "Method and Apparatus for Particle Analysis" 365/28.5

U.S. Pat. No. 5,561,515 October 1996 Hairston et al. "Apparatus for Measuring Particle Sizes and Velocities" 356/28

U.S. Pat. No. 5,679,907 October 1997 Ruck "Method and Device to Determine the Aerodynamic Diameter of Particles" 73/865.5

U.S. Pat. No. 5,701,012 December 1997 Ho "Fluorescent Biological Particle Detection System" 250/461.2

STATEMENT AS TO THE RIGHTS TO INVENTIONS MADE UNDER FEDERALLY-SPONSORED RESEARCH AND DEVELOPMENT

This invention was not made as part of any federally sponsored research.

REFERENCE TO MICROFICHE APPENDIX

None

BACKGROUND OF THE INVENTION

1. Field of the Invention

The present invention relates to the methods used for the measurement of aerosol particles. In particular, the present invention relates to a method that intermittently or continuously changes the aerodynamic cut at the inlet of an optical sensor and thus records the measured concentrations of airborne particles relative to specific aerodynamic particle sizes.

2. Description of the Related Art

The motion in air of airborne particles and their deposition onto surfaces depends primarily on their particle size. Density, shape, and surface characteristics of the particles also influence their airborne behavior and are usually combined with the physical particle size through the "aerodynamic particle diameter". A common method for determining the aerosol size distribution is to collect the aerosol particles on a filter and to subsequently size them under an optical or electron microscope. However, this method only yields the physical size, not the aerodynamic particle size.

A common method for dynamically measuring the concentration and size distribution of particles in the airborne state is by optical single particle size spectrometry. In this method, one particle at a time is passed through an illuminated view volume, and the light scattered by each particle is recorded as to its magnitude. An optical single particle counter using this method is usually calibrated with spherical, monodisperse test particles of known particle density and optical characteristics, such as polystyrene latex (PSL) spheres. However, most airborne particles have their own light scattering and absorption characteristics, so that the "optical particle diameter" measured by this method generally does not correspond to the "aerodynamic particle diameter".

When using the optical single particle counting method, the device embodying this method can be aerodynamically calibrated by placing an impaction stage at its inlet. The "aerodynamic cut" of this impaction stage can be determined by theory or experiment. Thus, one optical particle size of the optical single particle counter can be related to its equivalent aerodynamic particle size. In order to operate the optical single particle counter in the field, the impaction stage is removed from the inlet. If an optical single particle counter is to be calibrated over a wide particle size range, several impaction stages with different aerodynamic cut sizes need to be successively attached to the optical single particle counter's inlet. This is very time consuming.

A simpler dynamic optical particle sensing method is "aerosol photometry". In an aerosol photometer using this method, the optical view volume is larger than in an optical single particle counter, thus accommodating a cloud of particles. However, the output from such a device depends not only on the optical characteristics of the particles, but also on the size distribution of the particles, because the light scattered by each particle depends on its refractive index and size.

In the present invention, the aerodynamic cut is continuously or intermittently varied at the inlet of an optical sensor. This permits the dynamic calibration and determination of the aerodynamic particle size distribution by use of a relatively inexpensive optical device, such as an optical single particle counter or an aerosol photometer.

Another dynamic, but more complex and expensive method for determining the aerodynamic particle size distribution in situ is by accelerating the aerosol particles in a nozzle and then measuring the "time of flight" of each particle between two points. In a nozzle or other acceleration field, aerodynamic drag accelerates large particles to a lesser extent than small particles. Thus, in an acceleration field, the time of flight between two points is longer for large particles than for small particles. The difference is caused by the difference in aerodynamic drag. Thus, this method determines the particle size distribution relative to the aerodynamic particle size. In the following U.S. patents, the time of flight is measured and related to aerodynamic particle size through different techniques and geometric arrangements: U.S. Pat. Nos. 4,633,714; 5,296,910; 5,561,515; 5,679,907; and 5,701,012.

BRIEF SUMMARY OF THE INVENTION

The method of the present invention consists of drawing airborne particles through a device which continuously or intermittently changes the aerodynamic cut of the particles entering an optical sensor. The airborne particles can be any inert or viable airborne particles, including dust, fume, smoke, fog, mist, smoke, bacteria, pollen, fungal spores, and fragments of biological or non-biological material. Optical sensing is performed by optical single particle size spectrometry or by aerosol photometry. The aerodynamic cut is achieved by a rotating element that centrifugally removes particles larger than a specific size to the inner wall of the housing containing the rotating element. The rotating element may be one or more disc or propeller blades mounted on a rotating shaft, or an impeller with radial, forward-curved or backward-curved blades.

When an optical single particle counter is used as the optical sensor in this method, the optical single particle counter is first operated while the rotating element in the aerodynamic cut device is non-rotating. At that time, the optical single particle counter records the aerosol concentration in specific "optical particle diameter" ranges. The amount of light scattered or absorbed by a particle depends on its optical characteristics. Therefore, this "optical particle diameter" generally does not correspond to the "aerodynamic particle diameter". The calibration relative to aerodynamic particle size is performed in this invention while a constant aerosol particle size distribution is maintained, and the aerodynamic cut device continuously or intermittently increases its rotational speed. Each rotational speed corresponds to a specific aerodynamic cut size. The aerodynamic particle size of this aerodynamic cut decreases as the rotational speed increases. Thus, the optical particle size is related to its equivalent aerodynamic particle size for the aerosol being measured. Once an optical single particle counter is calibrated relative to aerodynamic particle size for a specific aerosol environment, the aerodynamic cut device can be removed and the optical single particle counter can be operated alone as long as the material characteristics of the aerosol particles do not change substantially.

If an aerosol photometer is used as the optical sensor for this method, the aerodynamic cut device becomes an integral part of the photometer, effectively turning the aerosol photometer into an aerosol size spectrometer. At the beginning of the measurement cycle, the rotating element in the aerodynamic cut device is also nonrotating. Thus, the aerosol photometer output at the beginning of the measurement cycle corresponds to the entire aerosol cloud passing through the aerosol photometer. As the rotating element in the aerodynamic cut device increases its rotational speed, the aerosol photometer output is reduced by the amount of aerosol particles removed in the aerodynamic cut device. Thus, the difference in signal output obtained when increasing the speed of rotation of the rotating element corresponds to the aerosol particles removed in the aerodynamic particle size range defined by the two rotating speeds. The aerosol particles that have passed through the aerosol photometer can be collected on a filter. Thus, the particle count, surface area, volume or mass on the filter can be related to the photometer signals.

With this invention, higher aerosol concentrations can be measured than with the more complex and expensive "time of flight" method, because in the "time of flight" method the processing time for each particle is much longer. When aerosol photometry is used for the optical sensing, the aerosol flow rate can be much higher than in the "time of flight" method. Thus, a much larger volume of air can be analyzed as to its aerodynamic particle concentration in specific aerodynamic size ranges.

Thus, one objective of this invention is to have an inexpensive means for calibrating an optical single particle counter with respect to the aerodynamic particle sizes of the aerosol particles being sampled, and to then use the optical single particle counter as an aerodynamic particle size spectrometer.

Another objective of this invention is to use this method as an integral part of an aerosol photometer so that the photometric output of the aerosol photometer can be related to specific aerodynamic particle sizes, thus turning the aerosol photometer into an aerodynamic particle size spectrometer.

Another objective of this method is to be able to measure higher concentrations of aerosol particles than is possible with the more complex and expensive "time of flight" method.

Another objective of this method is to be able to measure a larger volume of aerosol particles per unit of time than is possible with the more complex and expensive "time of flight" method.

BRIEF DESCRIPTION OF THE DRAWINGS

FIGS. 4A, 4B and 4C are graphical representations of a typical particle size distribution recorded by optical single particle size spectrometry while the invented method of aerodynamically cutting the incoming aerosol is applied.

DETAILED DESCRIPTION OF THE INVENTION

Figure 1A:
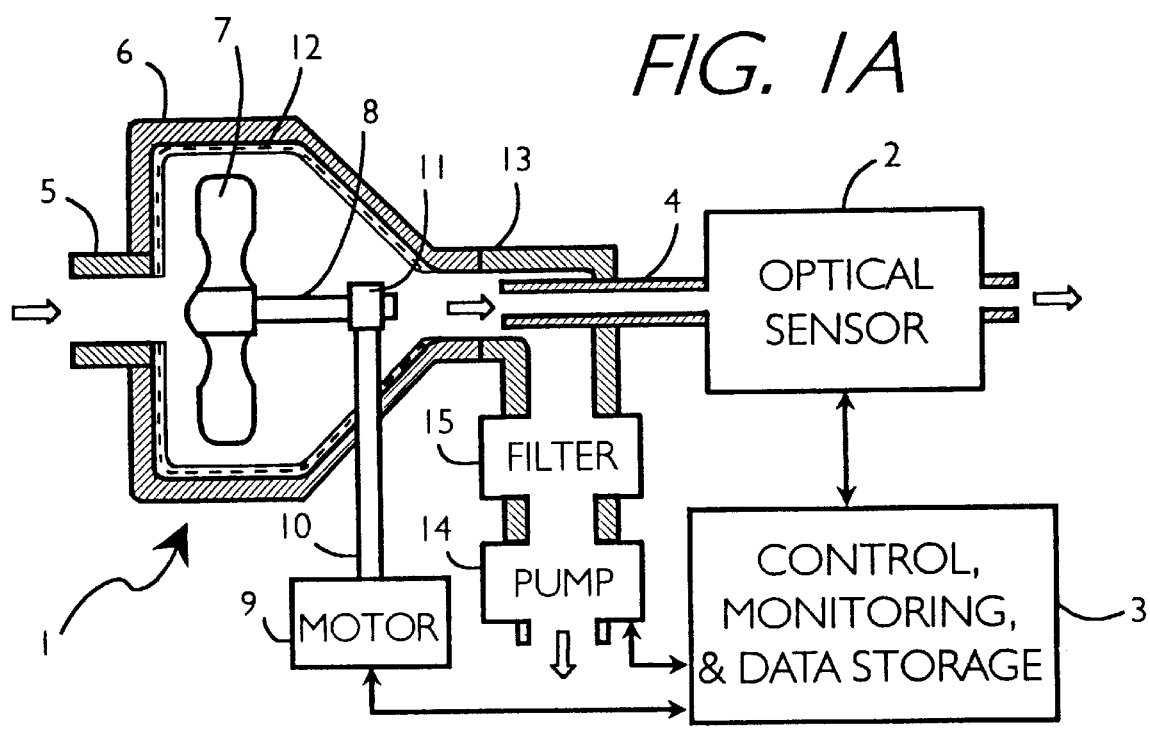
FIGS. 1A, 1B and 1C are schematic diagrams of the apparatus comprising the aerodynamic particle size analysis method.

The method of the present invention consists of drawing airborne particles through a device which continuously or intermittently changes the aerodynamic cut of the particle fraction entering an optical sensor. The airborne particles can be any inert or viable airborne particles, including dust, fume, smoke, fog, mist, smoke, bacteria, pollen, fungal spores, and fragments of biological or non-biological material. Optical sensing is performed by optical single particle size spectrometry or by aerosol photometry. The aerodynamic cut is achieved by a rotating element that centrifugally removes particles larger than a specific size to the inner wall of the housing containing the rotating element. The rotating element may be one or more disc or propeller blades mounted on a rotating shaft, or an impeller with radial, forward-curved or backward-curved blades.

As seen in FIG. 1, the invention comprises as main elements an aerodynamic cut device 1, an optical sensor 2, and a device performing control, monitoring and data storage functions 3. The aerodynamic cut device 1 is used to continuously or intermittently change the aerodynamic cut at the inlet 4 to the optical sensor 2 so that mostly particles below the aerodynamic cut size enter the optical sensor 2.

The method of achieving an aerodynamic cut is described by reference to FIG. 1A. Aerosol particles are drawn into the aerodynamic cut device 1 through inlet nozzle 5 which can be of any design compatible with sampling the aerosol particles under consideration. The aerosol particles pass through this inlet nozzle 5 into the housing 6 of the aerodynamic cut device 1. One or more blades 7 attached to shaft 8 rotate at a speed that can be changed continuously or intermittently from zero to a high number of revolutions per minute (rpm). The rpm depends on the aerodynamic cut size desired, and the size and design of the blades 7. The blades 7 are rotated by motor 9 whose shaft 10 moves shaft 8 through coupling 11. Coupling 11 is an example of how the motor 9 can rotate the blades 7. Other means of coupling can be used. The speed of the motor 9 is controlled by the control, monitoring and data storage unit 3.

The inside wall of the housing may have attached to it a coating of sticky substance 12 whose purpose is to retain the particles that are removed from the aerosol flow to the inner wall of the housing 6 by rotation of the blades 7. Sticky substance 12, such as oil or other adhesive material, is directly attached to the inner wall of housing 6. Sticky substance 12 may also be a removable insert with an adhesive coating on the side facing the blades 7.

The aerosol particles exiting from the aerodynamic cut device 1 are drawn toward the optical sensor 2 which samples from this aerosol flow through its inlet 4. Inlet 4 protrudes into the flow splitter 13 which by action of pump 14 removes the remaining aerosol. An optional filter 15 may be inserted upstream of pump 14. Pump 14 is also controlled by the control, monitoring and data storage unit 3.

The flow rate of the aerosol entering the aerodynamic cut device 1 is equal to the sum of the flow rates through pump 14 and inlet 4 of the optical sensor 2. In some circumstances, the flow splitter 13 can be eliminated so that the optical sensor 2 is directly coupled to the exit port of the aerodynamic cut device 1. In that case, the volumetric flow rate entering the optical sensor 2 through its inlet 4 equals the volumetric flow rate entering the aerodynamic cut device 1 through its inlet 5. Optical sensing is performed by optical single particle size spectrometry or aerosol photometry.

Figure 1B:
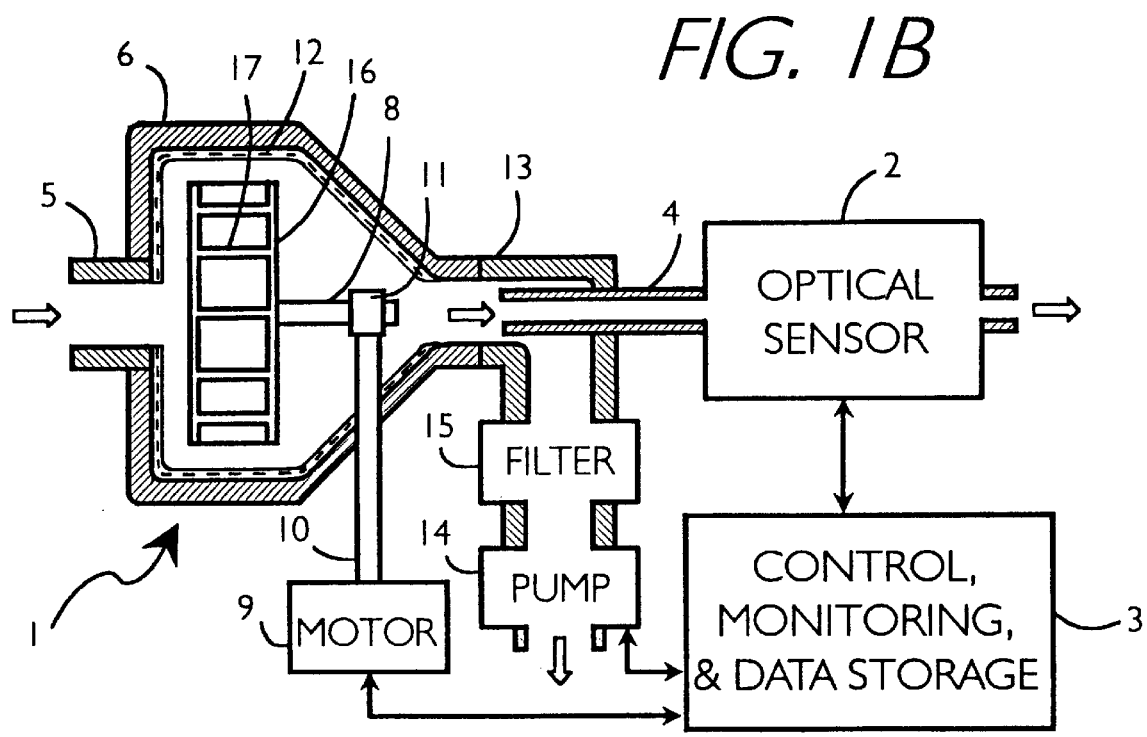

The blades 7 of FIG. 1A are replaced in FIG. 1B by an impeller 16 with radial, forward-curved or backward-curved blades 17. All other elements and their purposes in comprising the invented method are similar to those shown in FIG. 1A. Thus, FIG. 1A and FIG. 1B illustrate two means for centriftigally removing aerosol particles larger than the desired aerodynamic cut sizes by use of the aerodynamic cut device 1.

Figure 1C:
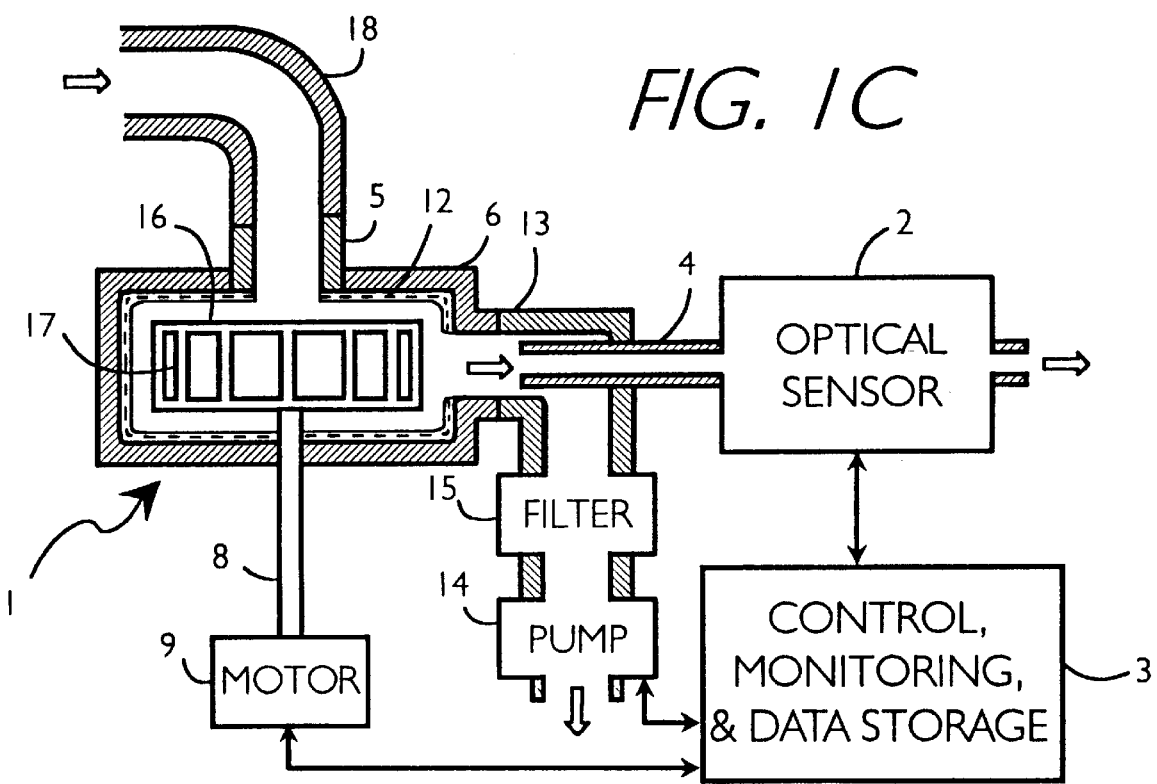

In FIG. 1C, further illustrating the new method, an impeller 16 with radial, forward-curved or backward-curved blades 17 is also used as the rotating device, similar to the one in FIG. 1B. However, in the illustration of FIG. 1C, the exit aerosol flow from the aerodynamic cut device 1 is perpendicular to the incoming aerosol flow. In this case, the motor 9 may be attached directly to shaft 8 without use of a coupling. All other elements and their purposes in comprising the invented method are similar to those shown in FIG. 1B. An optional inlet extension 18 with a gradual ninety degree bend can be attached to inlet 5 of the aerosol cut device 1, if the aerosol is to be sampled in the same direction as the inlet 4 axis of the optical sensor 2.

The optical sensing in the invented method can be performed by aerosol photometry. An aerosol photometer measures the amount of light scattered from a cloud of particles. The light scattering signal resulting from light illumination of a particle cloud depends primarily on the optical properties and the size of each particle in the view volume of the aerosol photometer. Thus, a standard aerosol photometer does not give an output signal relative to particle size. If an aerosol photometer is used as the optical sensor in the present invention, the aerodynamic cut device 1 effectively turns the aerosol photometer into an aerosol size spectrometer. The aerosol photometer output is related to aerodynamic particle size while the aerodynamic cut device 1 continuously or intermittently increases its rotational speed. Each rotational speed corresponds to a specific aerodynamic cut size. The aerodynamic particle size of this aerodynamic cut decreases as the rotational speed of the rotating element 7 or 16 increases.

Figure 2:
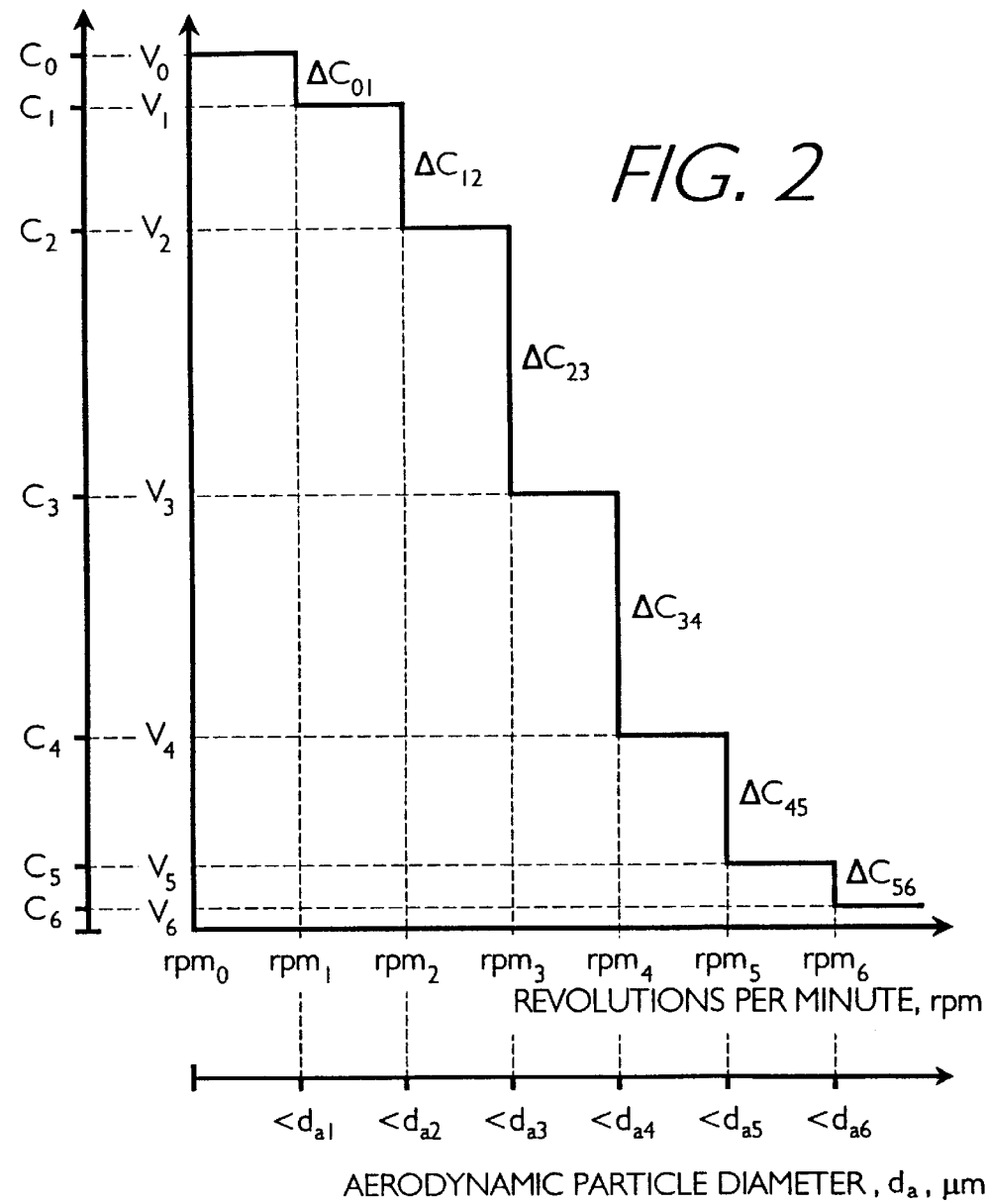
FIG. 2 is a graphical representation of typical raw and processed signals from use of the invention with aerosol photometry for optical sensing of the unremoved aerosol particles.

Typical output signals from an aerosol photometer, when used with the aerodynamic cut device 1 of this invention, are shown in FIG. 2. At the beginning of a measurement cycle, the rotating element 7 or 16 in the aerodynamic cut device 1 is nonrotating. Thus, it is rotating at zero revolutions per minute, rpm=0. This value is shown as $rpm_0$ on the abscissa of FIG. 2 and results in a light scattering signal from the entire particle cloud, exemplified as voltage $V_0$ on the ordinate of FIG. 2. The illustration of FIG. 2 is for intermittent increases in rpm of rotating element 7 or 16. When the rotating element 7 or 16 is set to $rpm_1>0$, the photometer voltage is reduced to $V_1$, if particles larger than the aerodynamic cut size at $rpm_1$ are present in the aerosol cloud entering the aerodynamic cut device 1. Thus, most of the remaining aerosol particles are less than aerodynamic particle diameter $d_{a1}$ in size, as shown on the second abscissa in FIG. 2. The relationship between rpm and aerodynamic particle diameter $d_a$ can be established theoretically, or experimentally by calibration with spherical test particles of known particle density, such as polystyrene latex (PSL) spheres. Subsequent increases in rpm decrease the aerodynamic cut size and correspondingly the photometer signal, if particles are removed by the aerodynamic cut device 1.

Figure 3:
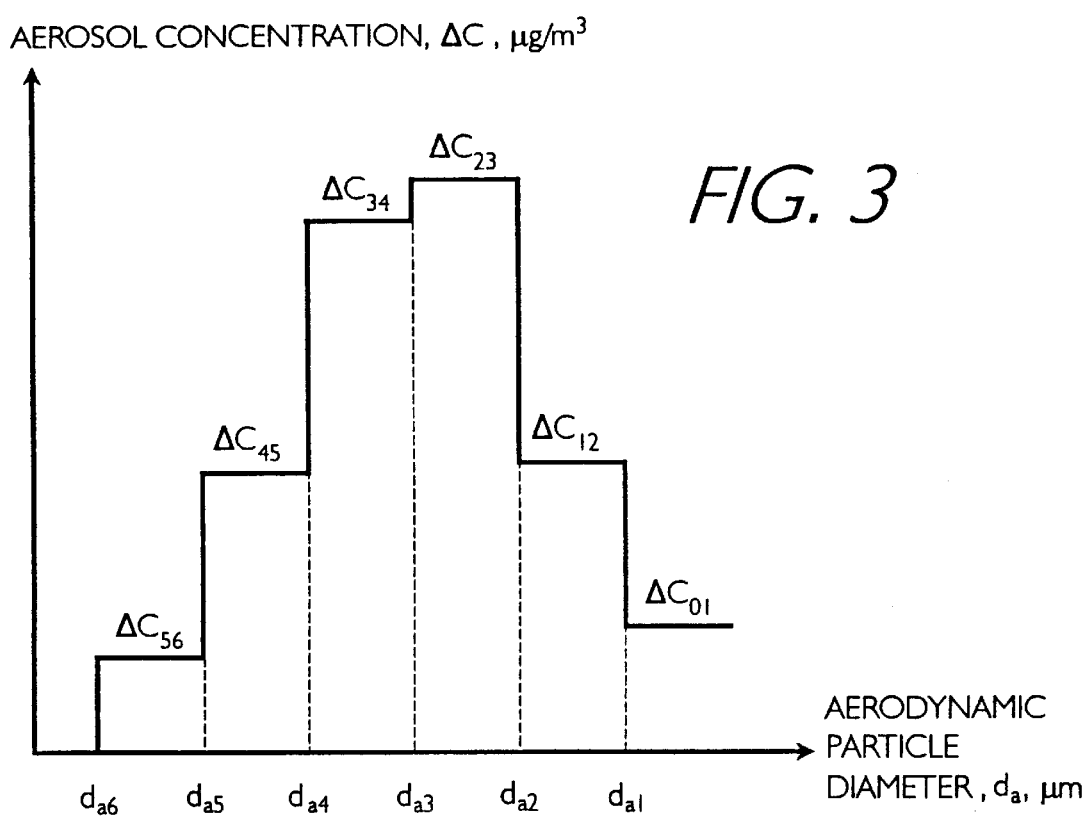
FIG. 3 is a graphical representation of a typical display of the aerodynamic particle size distribution when an aerosol photometer is turned into an aerodynamic particle size spectrometer through application of the invented method.

One of the means by which the decrease in photometer output voltage in a specific aerodynamic particle size range can be related to the particle count or particle mass in that aerodynamic particle size range is as follows. While maintaining a constant aerosol upstream of inlet 5 or 18 to the aerodynamic cut device 1, the aerosol particles that are not removed by the aerodynamic cut device 1 are collected on a filter. Conventional aerosol photometers generally allow insertion of a filter downstream of the photometric sensor. The difference in particle count or particle mass on the filters is then attributed to the difference in photometer voltage signal for the corresponding aerodynamic particle size range. Thus, the output signals of the aerosol photometer are calibrated relative to the rotational speed of the rotating element 7 or 16 in the aerodynamic cut device 1. This results in indications of the aerosol concentration c as a function of equivalent aerodynamic particle diameter $d_a$, as shown in FIG. 2. FIG. 2 exemplifies the aerosol concentration in $\mu g$ of particle mass per $m^3$ of air volume sampled. Aerosol photometer signal $V_0$ corresponds to aerosol concentration $c_0$, $V_1$ to $c_1$, $V_2$ to $c_2$ etc, as shown on the two ordinates in FIG. 2. The difference in aerosol concentration $\Delta c$ for a specific aerodynamic particle size range is also shown in FIG. 2. For instance, $\Delta c_{23}$ is the aerosol concentration in the aerodynamic particle size range between aerodynamic particle diameter $d_2$ and aerodynamic particle diameter $d_{a3}$. The aerosol concentration c in specific aerodynamic particle size ranges can then be plotted as a function of aerodynamic particle diameter $d_a$, as shown in FIG. 3. FIG. 3 is a typical output signal from an aerosol photometer when the invented method turns the aerosol photometer into an aerosol size spectrometer.

Another method that can be used for optical sensing in the invented method is optical single particle size spectrometry. In an optical single particle counter, the optical view volume is very small so that ideally only one particle at a time passes through the illuminated volume, resulting in a pulse of scattered light that is recorded by a sensor. The strength of each signal depends on the optical characteristics and the size of the particle passing through the view volume. An optical single particle counter is typically particle-size calibrated with spherical test particles of known optical characteristics, such as PSL spheres. The particle size distribution is then recorded as a function of "optical particle diameter".

When an optical single particle counter is used as the optical sensor 2 as part of the method described in this invention, the optical single particle counter is first operated while the rotating element 7 or 16 in the aerodynamic cut device 1 is non-rotating. At that time, the optical single particle counter records the aerosol concentration in specific "optical particle diameter" ranges. Since the amount of light scatterd or absorbed by a particle depends on its optical characteristics, the "optical particle diameter" generally does not correspond to the "aerodynamic particle diameter". The calibration relative to aerodynamic particle size is performed in this invention while a constant aerosol particle size distribution is maintained, and the aerodynamic cut device continuosly or intermittently increases its rotational speed. Each rotational speed corresponds to a specific aerodynamic cut size. The aerodynamic particle size of this aerodynamic cut decreases as the speed increases. Thus, the optical particle size is related to its equivalent aerodynamic particle size for the aerosol being measured. Once an optical single particle counter is calibrated relative to aerodynamic particle size for a specific aerosol environment, the aerodynamic cut device can be removed and the optical single particle counter can be operated alone as long as the material characteristics of the aerosol particles do not change substantially.

In this invention, the method for calibrating the optical single particle counter with respect to aerodynamic particle size is illustrated in FIG. 4. At the beginning of the calibration cycle, the optical single particle counter records the aerosol concentration as a function of the optical particle diameter $d_{opt}$ while the rotating element 7 or 16 in the aerodynamic cut device 1 is non-rotating. FIG. 4A illustrates a typical particle size distribution measured at $rpm_0=0$. The curve in FIG. 4A is fitted to the aerosol concentration data in specific optical particle size channels. The aerosol concentration is exemplified as the number of aerosol particles per $m^3$ of air volume sampled.

When the rotating element 7 or 16 in aerodynamic cut device 1 is rotated at $rpm_1>0$, the particles larger than the aerodynamic cut size corresponding to $rpm_1$ are removed by the aerodynamic cut device, and the particle size distribution is truncated, as illustrated in FIG. 4B. The optical particle diameter at which the truncated part of the particle size distribution is half of its original value can be defined as the aerodynamic cut diameter $d_{a1}$ corresponding to $rpm_1$. Other parts of the truncated curve may also be used to define the aerodynamic cut. As the rotational speed of the rotating element 7 or 16 is further increased to $rpm_2$, the particle size distribution curve may be truncated further, as shown in FIG. 4C.

Figure 5:
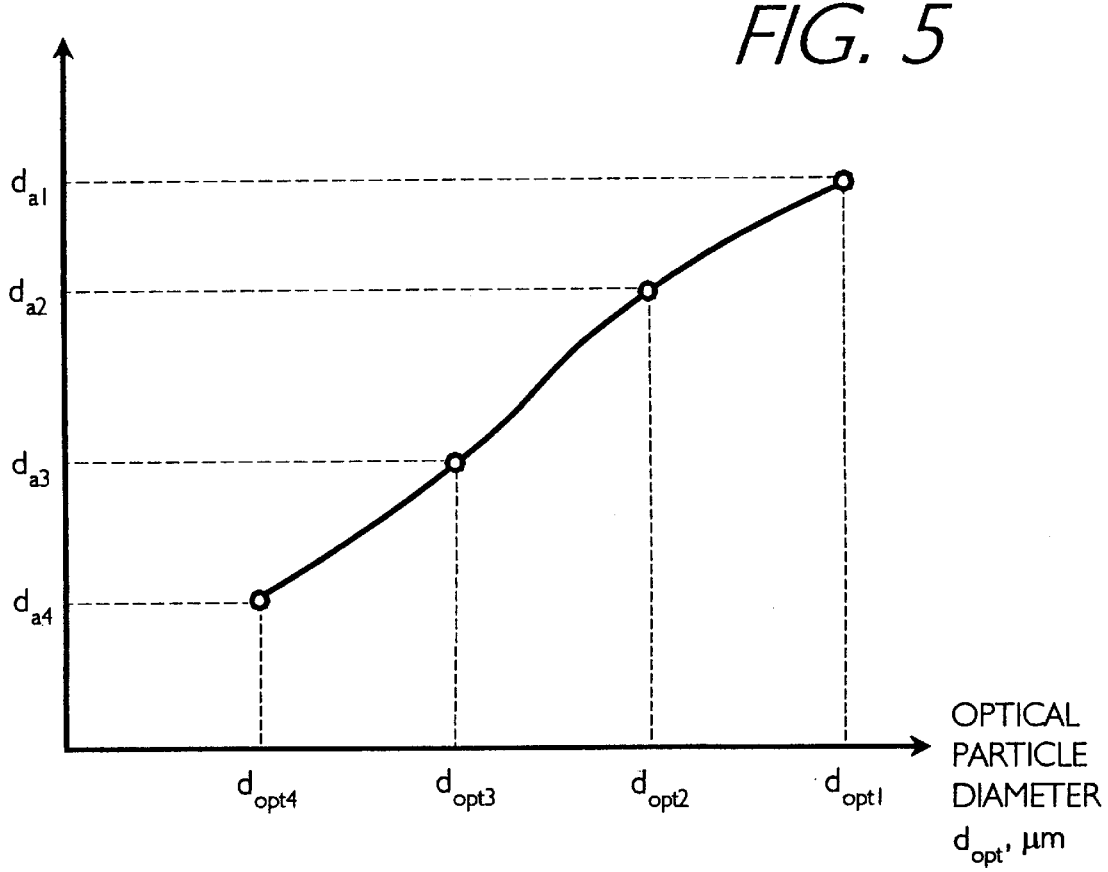
FIG. 5 is a graphical representation of the correspondence between aerodynamic particle size and optical particle size for an optical single particle counter sampling an aerosol environment.

The relationship between the optical particle diameter $d_{opt}$ at which the aerodynamic cut device 1 removes essentially all particles above a specific aerodynamic particle diameter $d_a$ is exemplified in FIG. 5. The calibration curve for the data in FIG. 5 is then entered into the memory of the optical single particle counter or the control, monitoring and data storage unit 3. Subsequent measurements of the aerodynamic particle size distribution are then made while the rotating element 7 or 16 in the aerodynamic cut device 1 is non-rotating, or the entire aerodynamic cut device 1 is removed from the inlet of the optical single particle counter. Renewed calibration is performed to confirm the validity of the previous one, or when the optical characteristics of the aerosol particles being sampled are considered to have changed significantly.

With this invention, higher aerosol concentrations can be measured than with the more complex and expensive "time of flight" method. In the "time of flight" method, the aerodynamic particle size distribution is determined in situ by accelerating the aerosol particles in a nozzle and then measuring the "time of flight" of each particle betweeen two points. In a nozzle or other acceleration field, aerodynamic drag accelerates large particles to a lesser extent than small particles. Thus, in an acceleration field, the time of flight between two points is longer for large particles than for small particles. The difference is caused by the difference in aerodynamic drag. Thus, the "time of flight". method determines the particle size distribution relative to aerodynamic particle size. Since the time of flight in these devices is usually longer than the single light scattering pulse in an optical single particle counter, the single particle counter can generally be operated at higher aerosol concentrations.

When aerosol photometry is used for the optical sensing, the aerosol flow rate can be much higher than in the "time of flight" method. Thus, a much larger volume of air can be analyzed as to its aerodynamic particle concentration in specific aerodynamic size ranges.

I claim as my invention:

1. A method for determining the concentrations of airborne particles as a function of their aerodynamic particle sizes, the method comprising the steps of:

air and airborne particles, herein referred to as aerosol, being drawn or pushed into an aerodynamic cut device;

said aerodynamic cut device containing a rotating element that at successively higher speeds makes aerodynamic cuts at successively smaller aerodynamic particle size by centrifugally removing particles larger than the respective aerodynamic cut;

said aerodynamic cut device having an exit opening from which the particles smaller than the aerodynamic cut size are sampled or pushed into an optical sensor;

said optical sensor recording the aerosol concentrations as a function of the aerodynamic particle sizes determined by said aerodynamic cut device.

2. The method defined in claim 1, wherein said rotating element comprises one or more disc or propeller blades mounted on a shaft, or an impeller with radial, forward-curved or backward-curved blades.

3. The method defined in claim 1, wherein the axis of said rotating element is either parallel or perpendicular to the axis of the inlet to said optical sensor.

4. The method defined in claim 1, wherein the rotational speed of said rotating element is continuously or intermittently increased from zero to a high number of revolutions per minute.

5. The method defined in claim 4, wherein increasing rotational speeds of said rotating element give aerodynamic cuts at decreasing aerodynamic particle sizes.

6. The method defined in claim 1, wherein said aerodynamic cut device removes particles larger than said aerodynamic cut size to the inner wall of said aerodynamic cut device.

7. The method defined in claim 6, wherein said inner wall is coated with a sticky substance for retaining removed particles or is covered with a removable insert with a sticky substance attached to the surface facing said rotating element.

8. The method defined in claim 1, wherein a flow splitter is attached to said exit opening of said aerodynamic cut device so that said optical sensor samples all or a fraction of the aerosol flow exiting from said aerodynamic cut device.

9. The method defined in claim 1, wherein said optical sensor measures the aerosol by aerosol photometry or by optical single particle size spectrometry.

10. The method defined in claim 9, wherein an aerosol photometer utilizing said method of aerosol photometry records the light scattering signals emitted by the aerosol particles as they exit from said aerodynamic cut device while said rotating element is continuously or intermittently changing its speed of rotation.

11. The method defined in claim 10, wherein the differences in said light scattering signals from said aerosol photometer are related to the particle count, surface, volume or mass in the aerosol size range corresponding to the speed of rotation of said rotating element in said aerodynamic cut device.

12. The method defined in claim 9, wherein an optical single particle counter utilizing said method of optical single particle size spectrometry records the particle size distribution as a function of aerodynamic particle size by relating the aerodynamic cuts obtained through operation of said aerodynamic cut device to the optical sizes of the optical single particle counter.

* * * * *

UNITED STATES PATENT AND TRADEMARK OFFICE
CERTIFICATE OF CORRECTION

PATENT NO. : 5,949,001

DATED : September 7, 1999

INVENTOR(S) : Klaus Willeke

It is certified that error appears in the above-identified patent and that said Letters Patent is hereby corrected as shown below:

Column 6, line 44 reads, "diameter d2" and should read --diameter da2--.

Signed and Sealed this

Twenty-seventh Day of March, 2001

*Attest:*

NICHOLAS P. GODICI

*Attesting Officer*   Acting Director of the United States Patent and Trademark Office